US010400081B2

(12) United States Patent
Gerges et al.

(10) Patent No.: US 10,400,081 B2
(45) Date of Patent: Sep. 3, 2019

(54) FOAMED POLYURETHANE POLYMERS FOR THE REGENERATION OF CONNECTIVE TISSUE

(71) Applicant: Tensive S.R.L., Milan (IT)

(72) Inventors: Irini Gerges, Milan (IT); Federico Martello, Milan (IT); Margherita Tamplenizza, Alessandria (IT); Alessandro Tocchio, Woodside, CA (US)

(73) Assignee: TENSIVE S.R.L., Milan (IT)

( * ) Notice: Subject to any disclaimer, the term of this patent is extended or adjusted under 35 U.S.C. 154(b) by 157 days.

(21) Appl. No.: 15/305,904

(22) PCT Filed: Apr. 15, 2015

(86) PCT No.: PCT/IB2015/052737
§ 371 (c)(1),
(2) Date: Oct. 21, 2016

(87) PCT Pub. No.: WO2015/162523
PCT Pub. Date: Oct. 29, 2015

(65) Prior Publication Data
US 2017/0044344 A1 Feb. 16, 2017

(30) Foreign Application Priority Data

Apr. 23, 2014 (IT) .............................. MI2014A0754

(51) Int. Cl.
| | |
|---|---|
| *C08J 9/08* | (2006.01) |
| *A61L 27/18* | (2006.01) |
| *C08G 18/08* | (2006.01) |
| *A61L 27/56* | (2006.01) |
| *A61L 27/12* | (2006.01) |
| *C08G 18/16* | (2006.01) |
| *C08G 18/40* | (2006.01) |
| *C08G 18/66* | (2006.01) |

(Continued)

(52) U.S. Cl.
CPC ................ *C08J 9/08* (2013.01); *A61L 27/12* (2013.01); *A61L 27/18* (2013.01); *A61L 27/56* (2013.01); *C08G 18/0847* (2013.01); *C08G 18/0852* (2013.01); *C08G 18/14* (2013.01); *C08G 18/163* (2013.01); *C08G 18/165* (2013.01); *C08G 18/4081* (2013.01); *C08G 18/6677* (2013.01); *C08G 18/73* (2013.01); *C08J 9/0066* (2013.01); *C08K 3/32* (2013.01); *C08G 2101/00* (2013.01); *C08G 2230/00* (2013.01); *C08J 2203/02* (2013.01); *C08J 2205/06* (2013.01); *C08J 2205/10* (2013.01); *C08J 2207/10* (2013.01); *C08J 2375/08* (2013.01); *C08K 2003/325* (2013.01)

(58) Field of Classification Search
CPC .......... A61L 27/12; A61L 27/18; A61L 27/56; C08G 18/0847; C08G 18/0852; C08G 18/14; C08G 18/163; C08G 18/165; C08G 18/4081; C08G 18/6677; C08G 18/73; C08G 2101/00; C08G 2230/00; C08J 9/0066; C08J 9/08; C08J 2203/02; C08J 2205/06; C08J 2205/10; C08J 2207/10; C08J 2375/08; C08K 3/32; C08K 2003/325; C08L 75/04
See application file for complete search history.

(56) References Cited

U.S. PATENT DOCUMENTS

| | | |
|---|---|---|
| 8,460,378 B2 | 6/2013 | Gogolewski |
| 2010/0068171 A1 | 3/2010 | Guelcher et al. |

(Continued)

FOREIGN PATENT DOCUMENTS

WO 2011015568 A1 2/2011

OTHER PUBLICATIONS

L.R. Snyder, "Classification of the Solvent Properties of Common Liquids", Journal of Chromatography, 1974, vol. 92, pp. 223-230.

(Continued)

*Primary Examiner* — John M Cooney
(74) *Attorney, Agent, or Firm* — Abelman, Frayne & Schwab

(57) ABSTRACT

The present invention relates to a method of synthesis and the use of foamed, cross-linked polyurethane polymers, as a three-dimensional support called a "scaffold" for cell cultures in vitro and for in vivo implantation for the regeneration of connective tissues such as adipose tissue, osteochondral tissue and bone tissue. In particular, the invention relates to a method of preparing polymers or foamed polyurethane co polymers, having improved hydrophilia, which involves the use of two types of catalyst, one for the cross-linking reaction and one for the foaming reaction and the use of at least one polar aprotic high-boiling solvent. Said method comprises the following steps in sequence: a) providing a solution of a polyol or a mixture of polyols in a solvent or mixture of solvents; b) heating the solution in step a) to a temperature higher than the softening temperature of the polymer precursors; c) optionally adding an organic or inorganic filler material; d) adding to the mixture in step c) an aliphatic poly-isocyanate or a mixture of poly-aliphatic isocyanates; e) adding to the mixture in step (d)) a porogenic additive; f) adding to the mixture in step e) simultaneously a cross-linking catalyst of polyols with poly-isocyanates and a foaming catalyst to form a foamed polyurethane polymer or co-polymer; g) isolating the foamed polyurethane polymer or co-polymer produced in step f).

21 Claims, 2 Drawing Sheets

Figure 1:
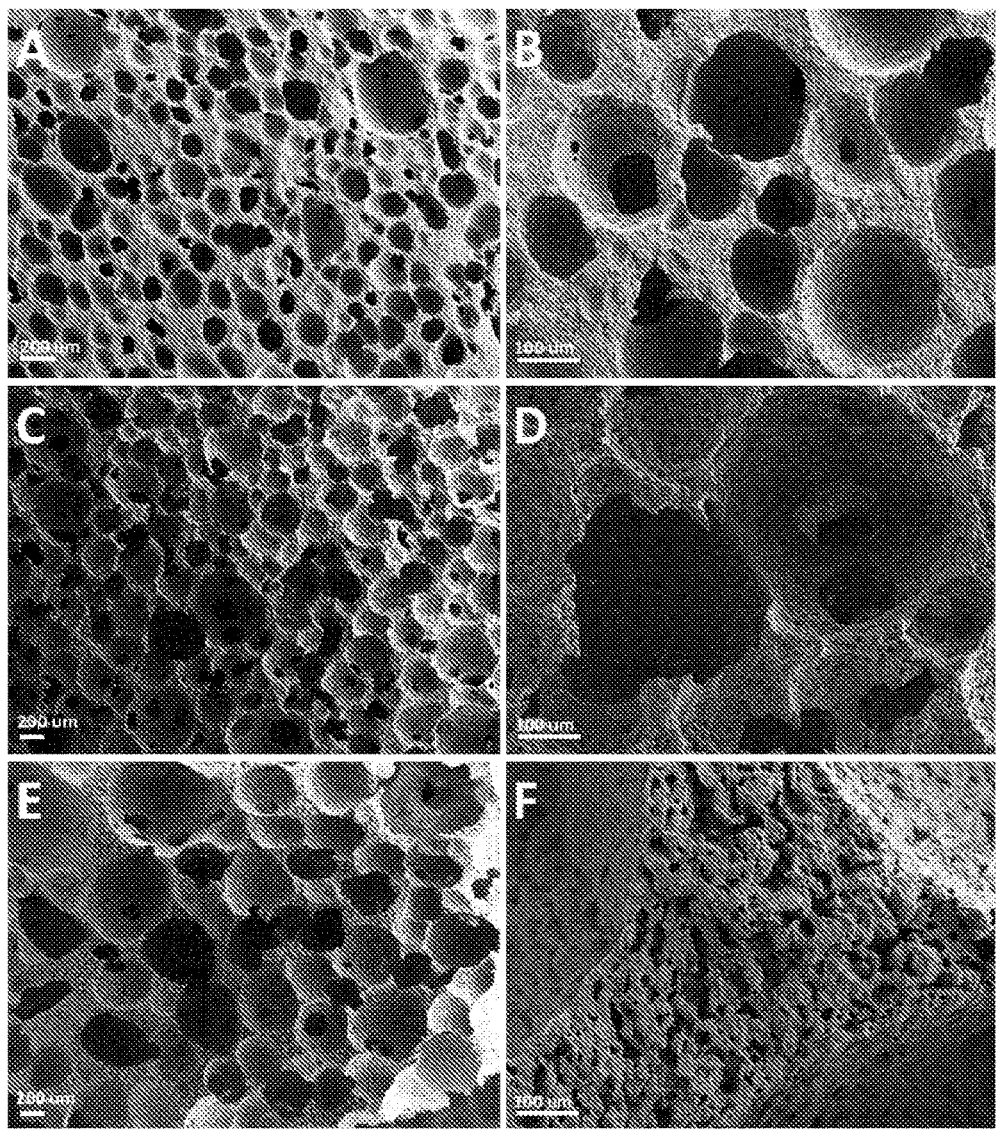

(51) Int. Cl.
*C08G 18/73* (2006.01)
*C08J 9/00* (2006.01)
*C08K 3/32* (2006.01)
*C08G 101/00* (2006.01)

(56) References Cited

U.S. PATENT DOCUMENTS

2012/0071576 A1\* 3/2012 Burdeniuc ......... C08G 18/1825
521/128
2013/0108821 A1 5/2013 Wiese et al.

OTHER PUBLICATIONS

Suresh S. Narine, "Physical Properties of Polyurethanes Produced from Polyols from Seed Oils: II. Foams", J. Amer. Oil Chem. Soc., 2007, vol. 84, pp. 65-72.

\* cited by examiner

FOAMED POLYURETHANE POLYMERS FOR THE REGENERATION OF CONNECTIVE TISSUE

RELATED APPLICATIONS

This application is a United States national phase application under 35 USC § 371 of PCT/IB2015/052737 filed on Apr. 15, 2015, and claims the benefit under 35 USC § 119 of Italian patent application number MI2014A000754 filed Apr. 23, 2015, the disclosures of which are both incorporated herein by reference in their entireties.

The present invention relates to a method of synthesis and the use of foamed, cross-linked polyurethane polymers, as a three-dimensional support called a "scaffold" for cell cultures in vitro and for in vivo implantation for the regeneration of connective tissues such as adipose tissue, osteochondral tissue and bone tissue.

The use of polymer materials in the biomedical field is the subject of attention from the scientific community working in the field of tissue engineering because of a number of advantages characterising this class of materials related to their biocompatibility, versatility, low cost and ease of production on an industrial scale.

Among the most interesting classes of synthetic polymers, polyurethanes have been the focus of many scientific studies, thanks to their outstanding mechanical properties, compared to other more commonly used categories such as polyesters.

The main problems hindering the application of polyurethanes in clinical medicine relate to the slow degradation of these materials in vivo, the toxicity of some degradation products and poor wettability.

For cross-linked, biodegradable and improved hydrophilicity polyurethane foams, it is helpful for method of synthesis to encourage:

I) the miscibility of the reactive components of varying viscosity, molecular weight and hydrophilic/hydrophobic affinity;
II) the control of the reaction kinetics of both the cross-linking and foaming reactions;
III) a homogeneous distribution of the gas bubbles, released in the polymer matrix by the foaming reaction before the solidification thereof due to cross-linking;
IV) a homogeneous distribution of the heat produced by the exothermic polyaddition reaction between the polyols and the polyisocyanates;
V) the complete elimination of the catalysts, added solvents and unreacted substances, without altering the overall physical and chemical properties of the foam, with particular attention to the economic and environmental aspects, thus minimising wastage of solvents and the costs related to the disposal thereof.

In some earlier patent publications it has been shown that some of the above requirements can be achieved by adopting conventional synthetic approaches based on:

The use of surfactants, to decrease the surface tension of the reactive mixture, commonly known as "pore-openers", of a hydrophobic nature (e.g. in WO2011015568 A1);
The use of oily and hydrophobic emulsifiers to solubilise the biodegradable polyester segments and polyisocyanates (e.g. in US 20100068171;
The use of polymer precursors, characterised by low glass transition temperatures (Tg), generally available in a liquid state at ambient temperature (25° C.) and with molecular weights not exceeding 3000 Da (e.g. in U.S. Pat. No. 8,460,378 B2).

The main problem with using oily surfactants and emulsifiers is the permanent reduction of the hydrophilic nature of the foams, due to the chemical structures of said oils which are rich in reactive hydroxyl groups and easily co-polymerizable by polyaddition with poly-isocyanates.

The reduction of the hydrophilic nature of the foams dramatically compromises the ability of the foams to favour cellular colonisation and the proliferation therein, in addition to reducing the degradation kinetics on account of the lack of wettability (Narine, Suresh s., et al. 2007).

On the other hand, the use of polymer segments of low Tg limits the choice of flexible "soft" or rigid "hard" segments and consequently limits the ability to manipulate the physical and chemical properties of the foams.

According to previous methods of synthesis, it is thus impossible to obtain cross-linked polyurethane foams, using solid or semi-solid (waxy) monomers or polymer precursors, on account of the lack of miscibility at ambient temperature and up to 60° C., in addition to the difficulty of activating the terminal groups of said polymer precursors in heterogeneous conditions.

One object of the present invention is therefore to obtain a method for the production of polyurethane foams to be used for the regeneration of both hard and soft connective tissue which makes it possible to overcome the drawbacks of the state-of-the-art methods.

Such a method is defined in the appended claims.

A further object of the invention are cross-linked, aliphatic polyurethane foams.

Further characteristics and advantages of the present invention will be more clearly comprehensible from the description given below of some embodiments, made by way of a non-limiting example with reference to the appended drawings:

FIG. 1—Micrographs of electron microscopy scanning SEM of Soft Foam 1 (A, B), Soft Foam 2 (C, D) and Soft Foam 3 (E, F), synthesised according to example 1 of the present invention.

Figure 2:
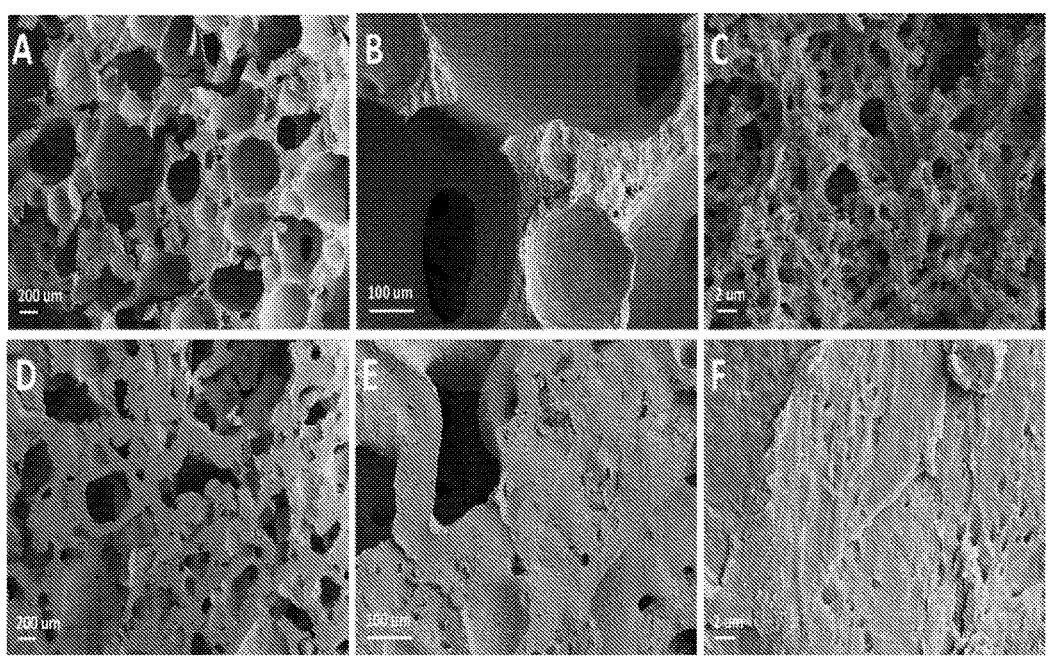

FIG. 2—Micrographs of electron microscopy scanning SEM of DexFoam 1 (A, B, C) and DexFoam 1' (D, E, F), synthesised according to example 2 of the present invention.

One object of the present invention is a method of preparing polyurethane foams having improved hydrophilia, which involves the use of two types of catalyst, one for the cross-linking reaction and one for the foaming reaction and the use of at least one polar aprotic high-boiling solvent. Said method comprises the following steps in sequence:

a) providing a solution of a polyol or a mixture of polyols in a solvent or mixture of solvents;
b) heating the solution in step a) to a temperature higher than the softening temperature of said polyols;
c) optionally adding an organic or inorganic filler material;
d) adding to the mixture in step c) an aliphatic poly-isocyanate or a mixture of aliphatic poly-isocyanates;
e) adding to the mixture in step (d)) a porogenic additive;
f) adding to the mixture in step e) simultaneously a cross-linking catalyst of polyols with poly-isocyanates and a foaming catalyst to form a polyurethane foam polymer or co-polymer;
g) isolating the polymer or co-polymer polyurethane foam produced in step f).

Step a)

The polyols that can be used in step a) of the method can be selected from the group consisting of:

1—polyalcohols, preferably glycerol, xylitol, mannitol, sorbitol, and galactitol;

2—monosaccharides, preferably glucose, fructose, and galactose;

3—oligosaccharides, preferably alpha-cyclodextrin, beta-cyclodextrin, gamma-cyclodextrin, and methyl-beta-cyclodextrin;

4—Polysaccharides, preferably dextrin, maltodextrin, dextran, agarose, pectin, starch, and cellulose;

5—Straight polyesters-polyols, preferably poly(epsilon-caprolactone)diol, poly(glycolide)diol (also known as dihydroxyl-terminated polyglycolic acid), poly(lactide)diol (also known as dihydroxyl-terminated polylactic acid), poly(epsilon-caprolactone-co-glycolide)diol, poly(lactide-co-glycolide)diol (also known as dihydroxyl-terminated poly lactic-co-glycolic acid) and poly(epsilon-caprolactone-co-lactide-co-glycolide)diol;

6—Branched, hyperbranched, or star-shaped polyesters polyols, preferably based on poly-hydroxyl-terminated poly(epsilon-caprolactone), poly-hydroxyl-terminated poly(glycolide) (also known as poly-hydroxyl-terminated poly-glycolic acid), poly-hydroxyl-terminated poly(lactide) (also known as poly-hydroxyl-terminated poly-lactic acid), poly-hydroxyl-terminated poly(epsilon-caprolactone-co-glycolide), poly-hydroxyl-terminated poly(lactide-co-glycolide) (also known as poly-hydroxyl-terminated poly lactic-co-glycolic acid), and poly-hydroxyl-terminated poly(epsilon-caprolactone-co-lactide-co-glycolide);

7—Polyether polyols or polyether epoxides, preferably poly(ethylene glycol), poly(propylene oxide) and poly(ethylene oxide)-block-poly(propylene oxide);

8—diamine-terminated polyalkylene oxide, preferably O,O'-Bis(2-aminopropyl)poly(propylene glycol)-block-poly(ethylene glycol)-block-poly(propylene glycol);

9—Block co-polymers terminated with hydroxyl groups, preferably poly(epsilon-caprolactone)-block-poly(ethylene glycol)-block-poly(epsilon-caprolactone)diol, poly(lactide)-block-poly(ethylene glycol)-block-poly(lactide)diol (also known as poly-lactic acid-block-poly(ethylene glycol)-block-dihydroxyl-terminated polylactic acid), poly(glycolide)-block-poly(ethylene glycol)-block-poly(glycolide) diol (also known as poly-glycolic acid-block-poly(ethylene glycol)-block-dihydroxyl-terminated polyglycolic acid), poly(epsilon-caprolactone-co-glycolide)-block-poly(ethylene glycol)-block-poly(epsilon-caprolactone-co-glycolide) diol, poly(lactide-co-glycolide)-block-poly(ethylene glycol)-block-poly(lactide-co-glycolide)diol (also known as poly-lactic acid-co-glycolic-block-poly(ethylene glycol)-block-dihydroxyl-terminated poly lactic-co-glycolic acid) and poly(epsilon-caprolactone-co-lactide-co-glycolide)-block-poly(ethylene glycol)-block-poly(epsilon-caprolactone-co-lactide-co-glycolide)diol.

In step a) only one polyol or a mixture of two or more polyols may be used, preferably chosen from the group listed above.

The solvent or mixture of solvents used in the method according to the present invention are preferably high-boiling solvents. The term "high-boiling solvent is taken to mean a solvent with a boiling temperature at least 15° C. above the softening temperature of the polyols used. For example, if the polyol has a softening temperature of 60° C., as is the case of poly (ethylene) glycol, the solvent will have a boiling point of at least 75° C. The solvent is thus selected based on the softening temperature of the polymer precursors used, as defined below.

The use of high-boiling solvents makes it possible to quickly dispose of the excess heat released during the cross-linking step, which helps to control the degree of porosity of the final polyurethane.

In preferred embodiments, the solvent or mixture of solvents is preferably a polar aprotic solvent having a Snyder's polarity index P greater than or equal to 5.5, in particular water miscible solvents.

Snyder's polarity index is a known classification parameter of solvents and can be calculated as described in L. R. Snyder, *Classification of the solvent properties of common liquids*, J. Chrom. Sci., 1978, 16, 223-234.

Solvents particularly suitable for the method of the invention are dimethylformamide (DMF), N,N'-dimethylacetamide (DMAc), dimethyl sulfoxide (DMSO) and acetonitrile (ACN).

Step b)

The softening temperature or softening point of the polyols is the temperature at which the polymer starts to change its state of aggregation from solid to liquid.

The softening temperature may be determined according to the standard ASTM D6493-11 (so-called "ring and ball" test).

Step b) is preferably conducted under stirring, more preferably by means of a mechanical stirrer. The stirring speed is preferably between 100 and 700 rpm, or between 200 and 700 rpm, more preferably between 300 and 700 rpm, even more preferably about 400 rpm.

The use of a reaction temperature higher than the softening temperature of the polymer precursors makes it possible to avoid the glass transitions of such materials and promote their miscibility with the other components of the reaction mixture. This makes it possible to avoid the use of oily surfactants, which undermine the wettability of polyurethane foam and consequent penetration of the liquids inside the pores.

Step c)

Although step c) is optional, the addition of a filler to the reaction mixture is preferred.

Preferably, the fillers used in the method of the invention are selected from the group consisting of:

inorganic fillers selected from beta-tri-calcium phosphate (TCP), hydroxyapatite (HA), calcium oxide ($CaO_2$), and magnesium hydroxide (Brucite $Mg(OH)2$);

organic fillers selected from lipid- or polymer-based micro- and nanoparticles of synthetic and/or natural origin, comprising cell growth and/or differentiation factors or drugs.

The addition of an appropriate filler makes it possible to improve the biological and chemical-physical properties of the polyurethane foams, preserving the original properties of said fillers.

The filler may be added to the reaction mixture in weight amounts ranging from 5% to 120%, preferably 5% to 50%, based on the weight of the polyols or polyol mixture.

The addition is always made under stirring, but preferably at a speed of between 200 and 500 rpm, more preferably around 300 rpm.

It has also been demonstrated experimentally that the addition of fillers in the manner provided for in this invention does not affect the degree of porosity and pore interconnection of the foam.

Step d)

For the purposes of the present invention, the polyisocyanate may be chosen from the group consisting of:

1—Aliphatic diisocyanates, preferably hexamethylene diisocyanate, methylene dicyclohexyldiisocyanate, isophorone diisocyanate, cyclohexane diisocyanate, methyl ester l-lysine diisocyanate, ethyl ester l-lysine diisocyanate, and ethyl ester l-lysine triisocyanate;

2—Aliphatic poly-isocyanates, preferably poly(epsilon-caprolactone)diisocyanate, poly(glycolide)diisocyanate (also known as diisocyanate polyglycolic acid), poly(lactide)diisocyanate (also known as diisocyanate polylactic acid), poly(epsilon-caprolactone-co-glycolide)diisocyanate, poly(lactide-co-glycolide)diisocyanate (also known as diisocyanate polylactic-co-glycolic acid), and poly(epsilon-caprolactone-co-lactide-co-glycolide)diisocyanate;

3—Straight, branched and hyperbranched polyesters terminated with isocyanate groups based on poly(epsilon-caprolactone), poly(glycolide) (also known as polyglycolic acid), poly(lactide)(also known as polylactic acid), poly(epsilon-caprolactone-co-glycolide), poly(lactide-co-glycolide) (also known as polylactic-co-glycolic acid), or poly(epsilon-caprolactone-co-lactide-co-glycolide);

4—Block co-polymers terminated with isocyanate groups, preferably poly(epsilon-caprolactone)-block-poly(ethylene glycol)-block-poly(epsilon-caprolactone)diisocyanate, poly(lactide)-block-poly(ethylene glycol)-block-poly(lactide)diisocyanate (also known as poly-lactic acid-block-poly(ethylene glycol)-block-poly-lactic acid diisocyanate), poly(glycolide)-block-poly(ethylene glycol)-block-poly(glycolide)diisocyanate (also known as poly-glycolic acid-block-poly(ethylene glycol)-block-polyglycolic acid diisocyanate), poly(epsilon-caprolactone-co-glycolide)-block-poly(ethylene glycol)-block-poly(epsilon-caprolactone-co-glycolide)diisocyanate, poly(lactide-co-glycolide)-block-poly(ethylene glycol)-block-poly(lactide-co-glycolide)diisocyanate (also known as poly-lactic acid-co-glycolic-block-poly(ethylene glycol)-block-poly-lactic-co-glycolic acid diisocyanate) and poly(epsilon-caprolactone-co-lactide-co-glycolide)-block-poly(ethylene glycol)-block-poly(epsilon-caprolactone-co-lactide-co-glycolide)diisocyanate.

One type of isocyanate or a mixture of two or more isocyanates may be used.

The intermediate di- or poly-isocyanate is used in default of molar ratio compared to the polyol or polyols used in synthesis.

Preferably, the addition of isocyanate is performed under stirring at speeds between 300 and 700 rpm, more preferably at about 400 rpm.

Step e)

The term "porogenic additive" is take to mean a compound able to react with the di- or poly-isocyanates releasing carbon dioxide inside the polymer foam during the cross-linking step.

Preferred porogenic additives for the purposes of the present invention are chosen between water and formic acid.

The porogenic additive is added in amounts ranging from 5% to 30% in weight with respect to the weight of the isocyanate intermediate.

Step f)

The simultaneous addition of a cross-linking catalyst and a foaming catalyst is an essential element of the present invention. This way it is in fact possible to make the two reactions, cross-linking and the release of carbon dioxide by the isocyanate groups, proceed in parallel in order to obtain a degree of expansion up to 10 times the initial volume before reaching the cross-linking point leading to the "gelation" of the polymer matrix.

The cross-linking catalyst is added to the reaction mixture in a weight ratio ranging from 0.05% to 1.5% with respect to the weight of the other components of the mixture including monomers, fillers, and solvents.

The foaming catalyst may be added to the reaction mixture in a weight ratio ranging from 0.01% to 1.5% with respect to the weight of the other components of the mixture including monomers, fillers, and solvents.

By varying the ratio of the cross-linking catalyst and the foaming catalyst the level of porosity and density of the polyurethane foam may be modulated.

In the manner just described it is thus possible to modulate the internal porosity of the polyurethane foam product. Two types of porosity should be considered useful to promote cell colonization within the polyurethane foams: microscopic porosity of 5-50 µm and macroscopic porosity of 50-1000 microns. For bone tissue, the size of the pores of the foams is between 50 and 800 microns, while for adipose tissue it is between 50 and 500 microns. The micro-porosity, between 5 and 50 microns, determines the ability of physiological fluids and cells of host tissue transported by them, to infiltrate the polymer matrix.

Accelerating the NCO/OH reaction compared to NCO/water reaction results in small-sized pores (20-50 microns) which are not interconnected, conversely if the NCO/water reaction is accelerated compared to NCO/OH large, heterogeneous pores (300-800 microns) which are interconnected are obtained, it is therefore appropriate for both reactions to proceed with comparable speed, in order to obtain the degree of porosity and interconnectivity desired.

The porosity of the polyurethane foams can be measured by mercury porosimetry analysis.

The exact ratio between the two catalysts and the amount thereof compared to the other components of the mixture must be determined experimentally each time depending on requirements and the intended use of the polyurethane foam.

Catalysts with a higher chemical selectivity towards the cross-linking reaction (hereinafter "NCO/OH") suitable for the purposes of the present invention may be selected from the group consisting of:

metal carboxylates, preferably bismuth, zinc, zirconium carboxylates, and mixed bismuth-zinc carboxylate, preferably bismuth neodecanoate and zinc citrate;

Iron(III) acetylacetonate;

manganese bis (2-ethylhexanoate);

organic derivatives of tin, preferably dibutyltin dilaurate (DBT), tin (II) 2-ethylhexanoate, dimethyltin carboxylate, dioctyltin carboxylate, dioctyltin mercaptoacetate, dibutyltin mercaptide, and dimethyltin mercaptide;

organic derivatives of titanium, preferably titanium ethyl acetoacetate and tetra-n-propyl titanate;

metal-oxides, preferably Magnesium ethoxide.

Catalysts with a higher chemical selectivity towards the reaction with the foaming agents (hereinafter "NCO/water") suitable for the purposes of the present invention may be selected from the group consisting of:

1,8-diazabicyclo[5.4.0]undec-7-ene (DBU);

1,4-diazabicyclo[2.2.2]octane (DABCO);

N,N-dimethylcyclohexylamine (DMCHA);

N,N-diethylethanamine (TEA); and

N,N,N',N'-tetramethylethylenediamine.

The cross-linking and stop time of the foaming is generally between 5 seconds and two minutes, or between about 5 seconds and 1 minute.

Step g)

The isolation and purification of the polyurethane foam produced in step f) may take place advantageously by extraction in low-boiling solvents for the high-boiling solvents, the residual reagents, the catalysts and any by-products formed in the reaction.

Preferably an extraction system with boiling solvent is used, more preferably a continuous extraction method.

Low-boiling solvents suitable for the purposes of the invention are for example chlorinated solvents such as chloroform and dichloromethane, heptane, hexane, cyclohexane, diethyl ether, petroleum ether, dioxane, acetonitrile, acetone, ethyl acetate.

Below are some examples of polyurethane foams suitable for use as a three-dimensional support, called a "scaffold", for the regeneration of hard and soft tissues.

The examples of synthesis are reported in comparative mode to emphasize the advantages that characterize the method of this invention, compared to previous traditional approaches, in particular:

Example 1: soft formulations made from cross-linked polyurethane ester ethers, synthesized maintaining unchanged: the amount of reagents; the solvent; the reaction temperature and the stirring speed of the mixture, but varying the ratios of the two cross-linking and foaming catalysts, to demonstrate the advantage of being able to finely control the degree of porosity and other physical-chemical properties of the foams.

Example 2: rigid formulations made from polyurethane ethers, synthesized keeping unchanged: the ratios between the reagents; the ratio of the catalysts; the reaction temperature and the stirring speed of the mixture, but varying the solvent used to dissolve and homogenize the reaction mixture, to demonstrate the advantage of using a polar aprotic high-boiling solvent (polarity index greater than 5.5) compared to other solvents having a lower polarity.

Example 3: rigid formulations made from polyurethane ester ethers synthesized maintaining unchanged: the ratios of the reagents, the ratios of the catalysts, the reaction temperature and stirring speed of the mixture, but with the only difference of using a polar aprotic high-boiling solvent (polarity index 6.4) in place of the lipophilic emulsifier/surfactant, emphasising the difference between their degree of water absorption.

Example 1—Synthesis of Soft Polyurethane Foam, Filled with Hydroxyapatite Containing Segments of Poly (Epsilon-Caprolactone-Co-Glycolide)-Block-Poly (Ethylene Glycol)-Block-Poly (Epsilon-Caprolactone-Co-Glycolide) Diol and Poly (Ethylene Glycol) and Cross-Linked with Glycerol and Xylitol, Identified by the Name: Soft Foam In a polypropylene (PP) container the following reagents are introduced:

1 g xylitol 1 g glycerol 9 g poly (epsilon-caprolactone-co-glycolide)-block-poly (ethylene glycol)-block-poly (epsilon-caprolactone-co-glycolide) diol, number-average molecular weight 13000 Da poly (ethylene glycol), number-average molecular weight 6000 Da 5.5 ml N,N'-dimethylformamide (DMF).

The temperature of the mixture containing the components listed above is raised to the softening temperature (Tg) of the macro-diols. The mixture is stirred, using a mechanical stirrer at a speed of 600 rpm for ten minutes before the addition of the filler (9 g of hydroxyapatite) under mechanical stirring at a speed reduced to 400 rpm. After 5 minutes, the stirring speed is restored to 600 rpm before adding 9 ml of hexamethylene diisocyanate.

The temperature of the mixture is brought to 40° C. before adding 2 g of an aqueous solution of xylitol to 50% (weight/weight) under continuous stirring at 600 rpm.

Lastly the catalyst solution is added consisting of:

1 g bismuth neodecanoate (Bi.Neo) and 1 g 1,4-diazobi-cyclo [2.2.2] octane (DABCO) and 5 ml DMF in the quantities indicated in table 1, based on the specific requirements of the foam, in terms of degree of porosity, expansion and density of the foam.

TABLE 1

Effect of changing the amount of the cross-linking and foaming catalysts on the physical properties and morphology of the foams: Soft Foam, synthesized according to example 1

| Formulation | DABCO (weight/weight) | Bi.Neo (weight/weight) (%) | Volume expansion (%) | Density kg/m$^3$ | Mean dimension of pores (μm) |
|---|---|---|---|---|---|
| Soft Foam1 | 0.4 | 0.5 | 500 | 250 | 50-300 |
| Soft Foam2 | 0.2 | 0.3 | 300 | 400 | 100-200 |
| Soft Foam3 | 0.4 | 0.1 | 440 | 270 | 100-700 |

The cross-linking and stop time of the expansion of the polyurethane foam is between 20 and 40 seconds after the addition of the catalysts.

Pieces of various sizes and geometries may be shaped/cut out from the untreated foam.

The purification of the foam for use in tissue engineering is performed by extraction by boiling with chloroform, applying a magnetic stirring of 800 revs per minute, with periodic change of solvent between 2 and 30 times, according to the size and quantity of foams in question.

The foams obtained according to this example are characterised by:

1. swelling index at 37° C. in phosphate buffered saline PBS 1× of 250%
2. permeability at 37° C. of $7.7*10^{-11}$ m$^2$
3. elastic modulus and compressive strength of 30 kPa and 377 N/m respectively.

The biocompatibility of Soft Foam1 and its ability to promote an adequate three-dimensional support for cellular colonization was demonstrated in vivo by a sub-dermal implant in a murine model for a period of 21 days. The foams showed minimal inflammatory response by the host organism with a very low encapsulation. The foams favoured an infiltration of tissue inside them, an excellent cell adhesion to the walls of the pores and a deposition of extracellular matrix (ECM).

Example 2—Synthesis of Rigid Polyurethane Foam, Filled with Hydroxyapatite, Cross-Linked with Dextran Containing Segments of Poly (Ethylene Glycol), Identified by the Name: DexFoam1

In a polypropylene (PP) container the following reagents are introduced:

10 g poly (ethylene glycol), number-average molecular weight 2000 Da 3 g dextran, number-average molecular weight 9000-11000 Da 3 g calcium stearate 23 ml of solvent.

Solvents Tested:

N,N'-dimethylformamide (DMF), (boiling point 153° C.; polarity index 6.4), in the case of DexFoam 1.

Ethyl acetate (EtOAc), (boiling point 77.1° C.; polarity index 4.4), in the case of DexFoam 1'.

The temperature of the mixture containing the components listed above is raised to the softening temperature (Tg) of the poly (ethylene glycols), i.e. around 60° C. The mixture is stirred, using a mechanical stirrer at a speed of 600 rpm for ten minutes before the addition of the filler (10 g of hydroxyapatite) under mechanical stirring at a speed reduced to 400 rpm. After 5 minutes, the stirring speed is restored to 600 rpm before adding 14 ml of hexamethylene diisocyanate.

The temperature of the mixture is brought to 40° C. before adding 2.4 ml of bi-distilled water under continuous stirring at 600 rpm.

Lastly, dibutyltin dilaurate and N,N,N',N'-tetramethylethylenediamine are simultaneously added, 400 µl of each.

The cross-linking and stop time of the expansion of the polyurethane foam is between 10 and 20 seconds after the addition of the catalysts.

Pieces of various sizes and geometries may be shaped/cut out from the untreated foam.

The purification of the foam for use in tissue engineering is performed by extraction by boiling with chloroform, applying a magnetic stirring of 400 revs per minute, with periodic change of solvent between 15 and 40 times, according to the size and quantity of foams in question.

The general characteristics of the foams obtained according to this example are shown in table 2.

TABLE 2

Effect of varying the solvent on the physical and morphological properties of the foams: Soft Foam, synthesized according to example 1

| Formulation | DexFoam 1 | DexFoam 1' |
|---|---|---|
| Solvent | DMF | EtOAc |
| Macro-porosity (mean diameter; um) | Regular interconnected 200-1000 um | Low and irregular |
| Micro-porosity (mean diameter; um) | Present, highly interconnected, 1-10 um | absent |
| Volume expansion (%) | 500 | 200 |
| Permeability (m2) | $4.7*10^{-11}$ | $2.5*10^{-10}$ |
| Degree of swelling (%) | 150 | 110 |
| Compression elastic modulus (MPa) | 4 | 4.5 |

The difference between the internal morphology of DexFoam 1 and DexFoam 1' is shown in FIG. 1.

The pictures show the effect of the solvents used in the synthesis on the internal morphology of the foams. The foam DexFoam 1' proves free of micro-porosity with low macro-porosity and interconnectivity. DexFoam 1 instead has macro- and micro-porosity in addition to interconnection between the pores.

Example 3—Synthesis of Rigid Polyurethane Foam, Filled with Hydroxyapatite Cross-Linked with Dextran and Containing Segments of Poly (Epsilon-Caprolactone-Co-Glycolide)-Block-Poly (Ethylene Glycol)-Block-Poly (Epsilon-Caprolactone-Co-Glycolide) Diol and Poly (Ethylene Glycol), Identified with the Name: DexFoam2

In a polypropylene (PP) container the following reagents are introduced:

3 g poly (ethylene glycol), number-average molecular weight 6000 Da 1.7 g dextran, number-average molecular weight 9000-11000 Da 9 g poly (epsilon-caprolactone-co-glycolide)-block-poly (ethylene glycol)-block-poly (epsilon-caprolactone-co-glycolide) diol, number-average molecular weight 13000 Da.

2 g calcium stearate

The amounts of solvent or emulsifier used are as follows:

25 ml N,N'-dimethylformamide (DMF), in the case of DexFoam 2.

5 g castor oil, in the case of DexFoam 2'.

The temperature of the mixture containing the components listed above is raised to the softening temperature (Tg) of the poly (ethylene glycols), i.e. around 60° C. The mixture is stirred, using a mechanical stirrer at a speed of 600 rpm for ten minutes before the addition of the filler (9 g of hydroxyapatite) under mechanical stirring at a speed reduced to 400 rpm. After 5 minutes, the stirring speed is restored to 600 rpm before adding 10 ml of hexamethylene diisocyanate.

The temperature of the mixture is brought to 40° C. before adding 1.5 ml of bi-distilled water under continuous stirring at 600 rpm.

Lastly, bismuth neodecanoate and N,N,N',N'-tetramethylethylenediamine are simultaneously added, 600 µl of each.

The cross-linking and stop time of the expansion of the polyurethane foam is between 20 and 40 seconds after the addition of the catalysts.

Pieces of various sizes and geometries may be shaped/cut out from the untreated foam.

The purification of the foam for use in tissue engineering is performed by extraction by boiling with chloroform, applying a magnetic stirring of 300 revs per minute, with periodic change of solvent between 15 and 40 times, according to the size and quantity of foams in question.

TABLE 2

Effect of using polar aprotic solvent compared to that of oily emulsifier: castor oil on water absorption and the permeability of the foams at 37° C.

| Formulation | DexFoam 2 | DexFoam 2' |
|---|---|---|
| Solvent/emulsifier | DMF | Castor oil |
| Macro-porosity (mean diameter; um) | Regular interconnected 200-1000 um | Low and irregular |
| Micro-porosity (mean diameter; um) | Present, highly interconnected, 1-10 um | absent |
| Volume expansion (%) | 450 | 360 |
| Permeability (m2) | $5.1*10^{-11}$ | $1.2*10^{-10}$ |
| Degree of swelling (%) | 160 | 105 |
| Compression elastic modulus (MPa) | 3.5 | 2.6 |

The advantages of the process of the invention are apparent and in part already discussed above.

A further advantage is the possibility of co-polymerization with reactive biodegradable segments, mainly based on polyesters or polysaccharides, of different degrees of polarity, ensuring miscibility without having to resort to the use of oily surfactants which compromise both the biocompatibility of the foams and their hydrophilic nature.

Moreover, the process is easily reproducible and can be transferred on an industrial scale without the need for special precautions.

Unlike conventional polyurethane foams studied in the past in the biomedical field, the degradation products of the polyurethanes foams of this patent are totally non-toxic, thanks to the exclusive use of aliphatic isocyanates in place of those more commonly used of the aromatic type.

The recycling of more than 90% of the solvents used is another important aspect of the invention, with a positive impact on the economics and the possibility of adaptation to production processes on an industrial scale.

A further object of the invention is the polymer or co-polymer polyurethane foam obtained using the method of the invention as outlined above.

Yet a further object of the invention is the polymers or co-polymer of the invention for use in the regeneration of soft or hard connective tissue.

Other applications and uses of the foams according to the invention are listed below:
- support for the in vitro cultivation of cells and/or tissues for the production of bioactive substances, for example: the cultivation of cells of the islets of Langerhans for the production of insulin
- support for the cultivation of cells or tissues in vitro for the study of bioreactive drugs or molecules or cosmetic products
- support for the cultivation of cells or tissues in vitro for the study of dietary supplements
- three-dimensional support for the cultivation of cells in vitro in dynamic conditions (bioreactor) for the following applications:
  1. Development of systems for tissue engineering.
  2. Development of in vivo implantable devices made from engineered cells and/or tissues, sown and cultivated in the foams
  3. Development of systems for studying and monitoring in vitro or in vivo specific tissues such as: tumor tissues, vascular tissue, etc.
  4. Development of alternative systems for in vivo studies for the validation of drugs, bioreactive molecules and in the field of cosmetics.

It is clear that only some particular embodiments of the present invention have been described, which the person skilled in the art may modify so as to adapt it to specific applications while remaining within the sphere of protection of the present invention.

The invention claimed is:

1. A method for the preparation of polymer or co-polymer polyurethane foams with improved hydrophilia, which involves the use of a catalyst for the cross-linking reaction and a catalyst for the foaming reaction, comprising the following steps in sequence:
   a) providing a solution of a polyol or a mixture of polyols in a solvent or mixture of solvents, in which said polyol or mixture of polyols is characterized by a softening temperature and the solvent is a high-boiling solvent having a boiling point of at least 15° C. higher than the softening temperature of said polyol or mixture of polyols;
   b) heating the solution in step a) to a temperature higher than the softening temperature of said polyol or mixture of polyols;
   c) adding to the mixture in step b) an aliphatic poly-isocyanate or a mixture of aliphatic poly-isocyanates;
   d) adding to the mixture in step c) a porogenic additive;
   e) adding to the mixture in step d) simultaneously a cross-linking catalyst of polyols with poly-isocyanates and a foaming catalyst to form a polymer or co-polymer polyurethane foam; and
   f) isolating the polymer or co-polymer polyurethane foam produced in step e).

2. The method according to claim 1, wherein the polyols in step a) of the method are selected from the group consisting of:
   1—polyalcohols;
   2—monosaccharides;
   3—oligosaccharides;
   4—polysaccharides;
   5—straight polyesters-polyols;
   6—branched, hyperbranched, or star-shaped polyesters polyols;
   7—polyether polyols or polyether epoxides;
   8—diamine-terminated polyalkylene oxide; and
   9—block co-polymers terminated with hydroxyl groups.

3. The method according to claim 1, wherein the high boiling solvent in step a) is a polar aprotic solvent with a Snyder's polarity index P greater than or equal to 5.5.

4. The method according to claim 1, wherein the solvent is selected from dimethylformamide (DMF), N, N'-dimethylacetamide (DMAc) and dimethyl sulfoxide (DMSO) and acetonitrile (ACN) or a mixture of the above solvents.

5. The method according to claim 1, further comprising, between steps b) and c), adding an organic or inorganic filler material to the reaction mixture.

6. The method according to claim 5, wherein the fillers are selected from the group consisting of:
   inorganic fillers selected from beta-tri-calcium phosphate (TCP), hydroxyapatite (HA), calcium oxide (CaO2), and magnesium hydroxide (Brucite Mg(OH)2); and
   organic fillers selected from lipid- or polymer-based micro- and nanoparticles of synthetic and/or natural origin, comprising cell growth and/or differentiation factors or drugs.

7. The method according to claim 6, wherein the filler is added to the reaction mixture in weight amounts ranging between 5% and 120%, based on the weight of the polyols or polyol mixture.

8. The method according to claim 1, wherein, in step d), the poly-isocyanate is selected from the group consisting of:
   1—Aliphatic diisocyanates;
   2—Aliphatic poly;
   3—straight, branched and hyperbranched polyesters terminated with isocyanate groups; and
   4—Block co-polymers terminated with isocyanate groups.

9. The method according to claim 1, wherein, in step d), the porogenic additive is selected from water and formic acid.

10. The method according to claim 1, wherein the porogenic additive is added in amounts ranging between 5% and 30% by weight with respect to the weight of the isocyanate intermediate.

11. The method according to claim 1, wherein, in step e), the cross-linking catalyst is added to the reaction mixture in a weight ratio ranging between 0.05% and 1.5% with respect to the weight of the other components of the mixture including monomers, fillers, and solvents.

12. The method according to claim 1, wherein, in step e), the foaming catalyst is added to the reaction mixture in a weight ratio ranging between 0.01% and 1.5% with respect to the weight of the other components of the mixture including monomers, fillers, and solvents.

13. The method according to claim 1, wherein the cross-linking catalyst is selected from the group consisting of:
   metal carboxylates;
   organic derivatives of tin;
   organic derivatives of titanium; and
   metal oxides.

14. The method according to claim 1, wherein the foaming catalyst is selected from the group consisting of:

1,8-diazabicyclo[5.4.0]undec-7-ene (DBU);
1,4-diazabicyclo[2.2.2]octane (DABCO);
N,N-dimethylcyclohexylamine (DMCHA);
N,N-diethylethanamine (TEA); and
N,N,N',N'-tetramethylethylenediamine.

15. The method according to claim 1, wherein the step f) comprises the purification of the foamed polyurethane produced in step e) by extraction in low-boiling solvents for the high-boiling solvents, the residual reagents, the catalysts and the possible by-products formed in the reaction.

16. The method according to claim 15, wherein said low-boiling solvents are selected from chloroform, dichloromethane, heptane, hexane, cyclohexane, diethyl ether, petroleum ether, dioxane, acetone, acetonitrile, and ethyl acetate.

17. The method according to claim 6, wherein the filler is added to the reaction mixture in weight amounts ranging between 5% and 50%, based on the weight of the polyols or polyol mixture.

18. The method according to claim 15, wherein said extraction in low-boiling solvents is a continuous extraction.

19. The method according to claim 2, wherein
1—polyalcohols are selected from the group consisting of glycerol, xylitol, mannitol, sorbitol, and galactitol;
2—monosaccharides are selected from the group consisting of glucose, fructose, and galactose;
3—oligosaccharides are selected from the group consisting of alpha-cyclodextrin, beta-cyclodextrin, gamma-cyclodextrin, and methyl-beta-cyclodextrin;
4—polysaccharides are selected from the group consisting of dextrin, maltodextrin, dextran, agarose, pectin, starch, and cellulose;
5—straight polyesters-polyols are selected from the group consisting of poly(epsilon-caprolactone)diol, poly (glycolide)diol (also known as dihydroxyl-terminated polyglycolic acid), poly (lactide) diol (also known as dihydroxyl-terminated polylactic acid), poly (epsilon-caprolactone-co-glycolide) diol, poly (lactide-co-glycolide) diol (also known as dihydroxyl-terminated poly lactic-co-glycolic acid) and poly (epsilon-caprolactone-co-lactide-co-glycolide) diol;
6—branched, hyperbranched, or star-shaped polyesters polyols are selected from the group consisting of polyesters polyols based on poly-hydroxyl-terminated poly (epsilon-caprolactone), poly-hydroxyl-terminated poly (glycolide), poly-hydroxyl-terminated poly (lactide), poly-hydroxyl-terminated poly (epsilon-caprolactone-co-glycolide), poly-hydroxyl-terminated poly(lactide-co-glycolide), and poly-hydroxyl-terminated poly (epsilon-caprolactone-co-lactide-co-glycolide);
7—polyether polyols or polyether epoxides are selected from the group consisting of poly(ethylene glycol), poly(propylene oxide) and poly(ethylene oxide)-block-poly(propylene oxide);
8—diamine-terminated polyalkylene oxide are selected from the group consisting of O,O'-Bis(2-aminopropyl) poly(propylene glycol)-block-poly(ethylene glycol)-block-poly(propylene glycol); and
9—block co-polymers terminated with hydroxyl groups are selected from the group consisting of poly(epsilon-caprolactone)-block-poly(ethylene glycol)-block-poly(epsilon-caprolactone)diol, poly(lactide)-block-poly(ethylene glycol)-block-poly(lactide)diol, poly(glycolide)-block-poly(ethylene glycol)-block-poly(glycolide)diol, poly(epsilon-caprolactone-co-glycolide)-block-poly(ethylene glycol)-block-poly(epsilon-caprolactone-co-glycolide)diol, poly(lactide-co-glycolide)-block-poly(ethylene glycol)-block-poly(lactide-co-glycolide)diol and poly(epsilon-caprolactone-co-lactide-co-glycolide)-block-poly(ethylene glycol)-block-poly(epsilon-caprolactone-co-lactide-co-glycolide)diol.

20. The method according to claim 8, wherein:
1—Aliphatic diisocyanates are selected from the group consisting of hexamethylene diisocyanate, methylene dicyclohexyldiisocyanate, isophorone diisocyanate, cyclohexane diisocyanate, methyl ester L-lysine diisocyanate, ethyl ester L-lysine diisocyanate, and ethyl ester L-lysine triisocyanate;
2—Aliphatic poly-isocyanates are selected from the group consisting of poly(epsilon-caprolactone)diisocyanate, poly(glycolide)diisocyanate, poly(lactide)diisocyanate, poly(epsilon-caprolactone-co-glycolide)diisocyanate, poly(lactide-co-glycolide)diisocyanate, and poly (epsilon-caprolactone-co-lactide-co-glycolide) diisocyanate;
3—straight, branched and hyperbranched polyesters terminated with isocyanate groups are selected from the group consisting of polyesters based on poly(epsilon-caprolactone), poly(glycolide), poly(lactide), poly(epsilon-caprolactone-co-glycolide), poly(lactide-co-glycolide), and poly(epsilon-caprolactone-co-lactide-co-glycolide); and
4—Block co-polymers terminated with isocyanate groups are selected from the group consisting of poly(epsilon-caprolactone)-block-poly(ethylene glycol)-block-poly(epsilon-caprolactone)diisocyanate, poly(lactide)-block-poly(ethylene glycol)-block-poly(lactide)diisocyanate, poly(glycolide)-block-poly(ethylene glycol)-block-poly(glycolide)diisocyanate, poly(epsilon-caprolactone-co-glycolide)-block-poly (ethylene glycol)-block-poly(epsilon-caprolactone-co-glycolide) diisocyanate, poly(lactide-co-glycolide)-block-poly (ethylene glycol)-block-poly(lactide-co-glycolide)diisocyanate, and poly(epsilon-caprolactone-co-lactide-co-glycolide)-block-poly(ethylene glycol)-block-poly (epsilon-caprolactone-co-lactide-co-glycolide) diisocyanate.

21. The method according to claim 13, wherein:
metal carboxylates are selected from the group consisting of bismuth, zinc, zirconium carboxylates, and mixed bismuth-zinc carboxylate, preferably bismuth neodecanoate and zinc citrate; Iron (III) acetylacetonate; manganese bis (2-ethylhexanoate);
organic derivatives of tin are selected from the group consisting of dibutyltin dilaurate (DBT), tin (II) 2-ethylhexanoate, dimethyltin carboxylate, dioctyltin carboxylate, dioctyltin mercaptoacetate, dibutyltin mercaptide, and dimethyltin mercaptide;
organic derivatives of titanium are selected from the group consisting of titanium ethyl acetoacetate and tetra-n-propyl titanate; and
metal-oxides are magnesium ethoxide.

* * * * *